(12) United States Patent
Neumann et al.

(10) Patent No.: US 8,313,729 B2
(45) Date of Patent: Nov. 20, 2012

(54) INTEGRATED PHOTOACTIVE SMALL MOLECULES AND USES THEREOF

(75) Inventors: William L. Neumann, St. Louis, MO (US); Raghavan Rajagopalan, Solon, OH (US); Dennis A. Moore, St. Louis, MO (US); Richard B. Dorshow, St. Louis, MO (US)

(73) Assignee: Medibeacon, LLC, St. Louis, MO (US)

( * ) Notice: Subject to any disclaimer, the term of this patent is extended or adjusted under 35 U.S.C. 154(b) by 565 days.

(21) Appl. No.: 12/528,630

(22) PCT Filed: Feb. 26, 2008

(86) PCT No.: PCT/US2008/002521
§ 371 (c)(1),
(2), (4) Date: Aug. 26, 2009

(87) PCT Pub. No.: WO2008/108944
PCT Pub. Date: Sep. 12, 2008

(65) Prior Publication Data
US 2010/0105899 A1    Apr. 29, 2010

Related U.S. Application Data

(60) Provisional application No. 60/892,286, filed on Mar. 1, 2007.

(51) Int. Cl.
*A61B 5/00* (2006.01)
*A61B 8/00* (2006.01)
*A61B 10/00* (2006.01)
*A61K 49/00* (2006.01)

(52) U.S. Cl. .......................... 424/9.1; 424/9.6
(58) Field of Classification Search ............... 424/9.6
See application file for complete search history.

(56) References Cited

U.S. PATENT DOCUMENTS

| | | | |
|---|---|---|---|
| 5,330,737 A | 7/1994 | Rajagopalan | |
| 5,518,888 A | 5/1996 | Waldman | |
| 5,602,236 A | 2/1997 | Rajagopalan | |
| 6,406,713 B1 | 6/2002 | Janoff et al. | |
| 2004/0053828 A1 | 3/2004 | Mayo et al. | |
| 2006/0172943 A1 | 8/2006 | Edelberg et al. | |

FOREIGN PATENT DOCUMENTS

| | | |
|---|---|---|
| JP | 2006-36678 | 2/2006 |
| WO | WO 95/01990 | 1/1995 |
| WO | WO 97/07131 | 2/1997 |
| WO | WO 99/44994 | 9/1999 |
| WO | WO 00/55114 | 9/2000 |
| WO | WO 03/077928 | 9/2003 |
| WO | WO 2004/002401 | 1/2004 |
| WO | WO 2006/010070 | 1/2006 |
| WO | WO 2006/071759 | 7/2006 |
| WO | WO 2007/106142 | 9/2007 |
| WO | WO 2007/149478 | 12/2007 |
| WO | WO 2007/149479 | 12/2007 |

OTHER PUBLICATIONS

Cacciari et al., "Non Peptidic $\alpha_v\beta_3$ Antagonists: Recent Developments", Current Medicinal Chemistry, 2005, 12, pp. 51-701.
Cheng et al., "Near-infrared fluorescent RGD peptides . . . ", Bioconjug. Chem., 2005, 16(6), pp. 1433-1441.
Eaton et al., "The Anomalous electronic Properties of Azulenes", Mol. Photochem., 1(4), 1969, pp. 347-358.
Ecker et al., "Identification of Ligand-Binding . . . ", Molecular Pharmacology, 61(3), 2002, pp. 637-648, XP 002498099.
Garvin et al., "Phenamil: An Irreversible Inhibitor of Sodium . . . ", Journal of Membrane Biology, 87, 1985, pp. 45-54, XP 008094352.
Guccione et al., "Molecular imaging and therapy directed . . . ", IEEE Eng. Med. Biol. Mag., 2004, 23(5), pp. 50-56.
Gündisch et al., "Synthesis and Evaluation of Diazine containing Bioisoteres . . . ", Bioorganic & Medicinal Chemistry, 9, 2001, pp. 2683-2691, XP 002498100.
Gurfinkel et al., "Quantifying molecular specificity of alphavbeta3 integrin-targeted . . . ", J. Biomed. Opt., 2005, 10(3), pp. 034019-1-034019-9.
Hassan et al., "Overview Biomedical Applications of Fluorescence Imaging in Vivo", Comparative Medicine, 54(6), 2004, pp. 635-644.
Heinisch et al., "On the Bioisosteric Potential of diazines: Diazine Analogues . . . ", J. Med. Chem., 1996, 39, pp. 4058-4064, XP 002930170.
Horn et al., "Sunthesis of a Tetradentate Oxorhenium(V) . . . ", J. Org. Chem., 1997, 62, pp. 6290-6297.
Houston et al., "Quality analysis of in vivo near-infrared fluorescence and conventional . . . ", J. Biomed. Opt., 2005, 10(5), pp. 054010-2-054010-11.
Hunter et al., "Single Isomer Technetium-99m . . . ", Bioconjugate Chem . . . , 2000, 11, pp. 175-181.
Jain, "Barriers to Drug Delivery in Solid Tumors", Scientific American, 1994, pp. 58-65.
Kim et al., "Self-Assembling of Aminopyrazine Fluorescent Dyes . . . ", Dyes and Pigments, 39(4), 1998, pp. 341-357.
Kim et al., "Self-Assembling of Aminopyrazine Fluorescent Dyes . . . Part 2", Dyes and Pigments, 41, 1999, pp. 183-191.
Licha et al., "Optical imaging in drug discovery and diagnostic applications", Advanced Drug Delivery Reviews, 57, 2005, pp. 1087-1108.

(Continued)

*Primary Examiner* — Michael G Hartley
*Assistant Examiner* — Melissa Perreira
(74) *Attorney, Agent, or Firm* — Dennis A. Bennett; Gale W. Starkey

(57) ABSTRACT

This invention is directed to the general method of transforming non-photoactive bioactive small molecule compounds of known structure and function into photoactive analogs of the small molecules which exhibit both photoactivity and the original biological targeting activity. The general method for the design of the photoactive analogs of the small molecules includes: (a) selecting a desired bioactive molecule; (b) identifying the region of the molecule that contains an aromatic or a heteroaromatic motif; and (c) either replacing said motif with a photoactive functional group of similar size, or modifying said motif to make it photoactive. Other aspects include photoactive analog compounds and photodiagnostic and phototherapeutic uses thereof.

5 Claims, 7 Drawing Sheets

OTHER PUBLICATIONS

Miyata et al., "Synthesis and Properties of a New Fluorescent Bicyclic . . . ", Organic Letters, 2006, 8(8), pp. 1545-1548.

Nothnick, Expert Opinion Ther. Targets, 2004, 8(5), "Novel targets for the treatment of endometriosis", pp. 459-471.

Nozoe et al., "Some Synthetic Applications of 3-Carbosy-4-carbosy-methyltropolone", Tohoku Diagaku Hisui Yoeka Kagaku Kankyusho Hokoku, 1961, 10, pp. 199-211.

Sandler et al., "Fluorescent Profiling of Natural Product Producers", J. Am. Chem. Soc., 2005, 127, pp. 9320-9321.

Schneider et al., "A novel peptide, PLAEIDGIELTY, for targeting of . . . ", FEBS Letters 429, 1998, pp. 269-273.

Shah et al., "Molecular Optical Imaging: Applications Leading . . . ", NeuroRx, 2(2), 2005, pp. 215-225.

Shirai et al, "Syntheses and Fluorescent Properties . . . ", Dyes and Pigments, 39(1), 1998, pp. 49-68.

Skaddan et al., "Integrated "3+1" Oxorhenium(V) Complexes . . . ", Bioconjugate Chem., 1999, 10, pp. 119-129.

Solban et al., "12 Targeted Optical Imaging and Photodynamic Therapy", Ernst Schering Research Foundation, Workshop 49, pp. 229-258, 2005.

Vazquez et al., "6-N,N-Dimethylamino-2,3-naphthalimide: A New Environment . . . ", J. Med. Chem., 2006, 49, pp. 3653-3658.

Wentrup et al., "Sunthesis of 1-Azaazulene and Benz(a)azulene by Carbene Rearrangement", J. Am. Chem. Soc., 1984, 106, pp. 3705-3706.

Zimcik et al., "Synthesis and studies on photodynamic . . . ", Journal of Photochemistry and Photobiology A. Chemistry, 155, 2003, pp. 127-131.

INTEGRATED PHOTOACTIVE SMALL MOLECULES AND USES THEREOF

RELATED APPLICATIONS

This application claims priority to U.S. provisional application Ser. No. 60/892,286 filed on 1 Mar. 2007 entitled "INTEGRATED PHOTOACTIVE SMALL MOLECULES AND USES THEREOF".

FIELD OF THE INVENTION

This invention relates generally to optical imaging, visualization, and phototherapy. More particularly, the invention relates to the structural integration of a photoactive functional unit into a bioactive small molecule.

BACKGROUND

Publications are referenced throughout the specification in parenthesis. Full citation corresponding to each reference is listed following the detailed description. The disclosures of these publications are herein incorporated by reference in their entireties in order to describe fully and clearly the state of the art to which this invention pertains.

Molecules absorbing, emitting, or scattering light in the visible, near-infra red (NIR), or long-wavelength (UV-A, >300 nm) region of the electromagnetic spectrum are useful for optical tomography, optical coherence tomography, fluorescence endoscopy, photoacoustic technology, sonofluorescence technology, light scattering technology, laser assisted guided surgery (LAGS), and phototherapy. The high sensitivity associated with fluorescence phenomenon parallels that of nuclear medicine, and permits visualization of organs and tissues without the negative effects of ionizing radiation. Targeted delivery to a particular site in the body of diagnostic and therapeutic agents (generally referred to as "haptens," "effectors," or "functional units"), such as fluorophores, photosensitizers, radionuclides, paramagnetic agents, and the like, continues to be of considerable demand in diagnosis, prognosis, and therapy of various lesions (Hassan et al., Licha et al., Shah et al., Vasquez et al., and Solban et al.). The conventional targeting method, referred to as "bioconjugate approach" or "pendant design" involves chemical attachment of these agents to bioactive carriers which target a particular site in the body. In the bioconjugate approach, the two units can exist and function independently wherein the functions of targeting and imaging/therapy may be separable. Bioactive carriers include small molecule drugs, hormones, peptidomimetics, enzyme inhibitors, receptor binders, receptor antagonists, receptor agonists, receptor modulators, DNA binders, transcription factors, inhibitors of the cell cycle machinery, transduction molecules, inhibitors of protein-protein interactions, inhibitors of protein-biomacromolecule interactions, macromolecular proteins, polysaccharides, polynucleotides, and the like. The bioconjugate approach has been explored extensively over the past several decades, and has met with moderate success, particularly in tumor detection, when medium and large size carriers (c.a. molecular weight >1000 Daltons) are employed (Licha et al. and Shah et al.). This is because attachment of dyes, drugs, metal complexes, or other effector molecules to macromolecular carriers such as antibodies, antibody fragments, or large peptides does not greatly alter the bioactive targeting properties; i.e., the bioconjugate is still able to bind to the receptor effectively. However, this approach does have some serious limitations in that the diffusion of high molecular weight bioconjugates to tumor cells is highly unfavorable, and is further complicated by the net positive pressure in solid tumors (Jain et al.). Furthermore, many dyes tend to form aggregates in aqueous media that lead to fluorescence quenching.

A need therefore exists for photoactive small molecules that also have bioactive targeting capabilities. However, a problem in designing small molecule bioconjugates is that the binding of a diagnostic or therapeutic agent to a targeted receptor is often observed to be severely compromised when the sizes of the diagnostic or therapeutic agent and the bioactive targeting carrier are similar (Hunter et al.). Thus, substituting a large functional unit such as a dye or a photosensitizer into small molecule drugs, presents a formidable challenge. In order to overcome this problem, methods (referred to as "integrated approach" or "internal bifunctional approach") have been practiced wherein a radionuclide metal ion is incorporated into a steroid or morphine alkaloid framework such that the molecular topology of the original drug and the corresponding radionuclide mimic are very similar (Rajagopalan, U.S. Pat. No. 5,330,737; Rajagopalan, U.S. Pat. No. 5,602,236, and Hom et al.). In contrast to the bioconjugate approach described above, both functions of the integrated unit (e.g., targeting and imaging/therapy) are inseparable. The integrated approach is based on the principle that antibodies, enzymes, and receptors are multispecific and will bind to any molecule that is topologically similar to a natural antigen, substrate, or ligand. Previous work on steroid mimics confirm that integrating a metal ion into natural receptor ligands is a viable strategy for selective delivery of diagnostically and therapeutically useful radionuclides to target tissues (Hom, et al. and Skaddan et al.). This integrated design incorporates a single-atom isosteric substitution of a functional unit into a molecular framework. However, substituting a large functional unit such as a dye or a photosensitizer into small molecule drugs, peptides, pseudopeptides, or peptidomimetics presents a formidable challenge. While transformation of a nucleoside to fluorescent nucleoside has been previously reported (Miyata et. al.), the peak electronic spectra (absorption, excitation, and emission) remained in the UV region. In addition, this transformation is limited to this single nucleoside use.

SUMMARY

Among the various aspects of the present invention, therefore, is the provision of an integrated photoactive analog of a non-photoactive bioactive molecule, methods of making the same, and diagnostic and therapeutic uses thereof.

In one aspect, the present invention is directed to a method of generating an integrated photoactive analog of a non-photoactive bioactive molecule. The method includes replacing a non-photoactive functional group of the non-photoactive bioactive molecule with a photoactive functional group.

In another aspect, the invention is directed to a method of performing a diagnostic procedure on a patient. The method comprises administering an effective diagnostic amount of an integrated photoactive analog of a non-photoactive bioactive molecule to a patient.

In another aspect, the invention is directed to a method of performing a phototherapeutic procedure on a patient. The method comprises administering a therapeutically effective amount of an integrated photoactive analog of a non-photoactive bioactive molecule to a patient and irradiating the patient with a wavelength of light that causes photofragmentation of the molecule.

In still another aspect, the invention is directed to integrated photoactive small molecules and integrated photoactive small molecule integrin antagonists such as $\alpha_v\beta_3$ and $\alpha_5\beta_1$ antagonists.

Other aspects and features of this invention will be in part apparent and in part pointed out hereinafter.

DETAILED DESCRIPTION OF THE INVENTION

Figure 1A:
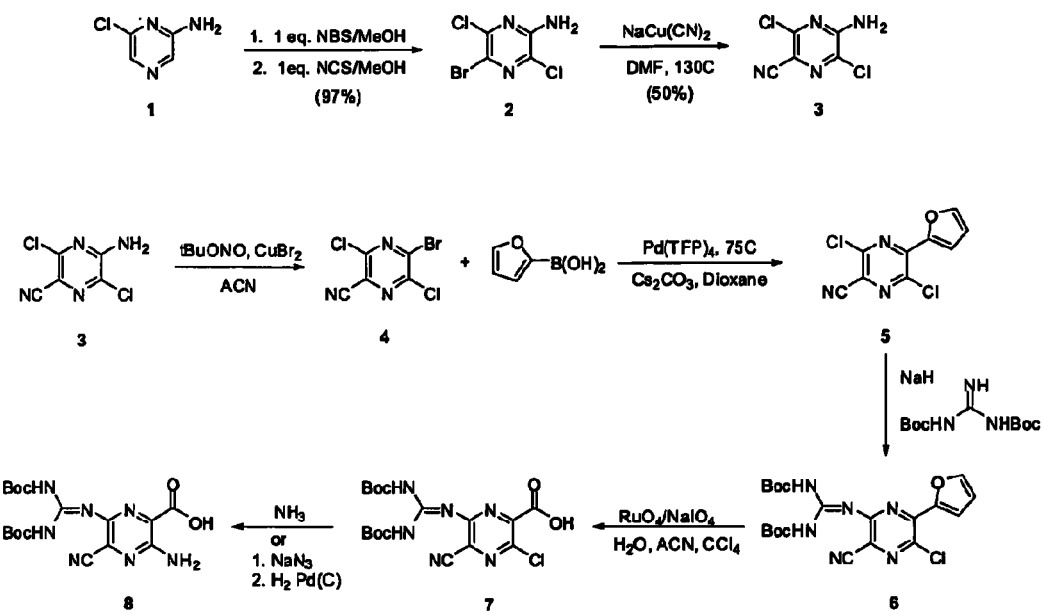
FIGS. 1A and 1B. Synthesis of Integrated Photoactive $\alpha_v\beta_3$ Antagonist Compound 14.

The present invention relates to the method of making and the use of integrated photoactive analogs (hereinafter referred to as "integrated photoactive analogs" or simply "analogs") of non-photoactive bioactive small molecules. Integrated photoactive analogs may be made by replacing a non-photoactive functional group of a non-photoactive bioactive small molecule with a photoactive moiety of similar size and molecular topology. The integrated photoactive analog can be administered to a patient and utilized as a biooptical diagnostic contrast agent and/or a phototherapeutic agent. In one embodiment, the integrated photoactive analog targets a specific tissue, cell, receptor, and the like in a patient. In one example, the analog targets a diseased tissue, cell, receptor, and the like in a patient.

The integrated photoactive analogs of the present invention have absorption, excitation, and emission maximum wavelengths in the near-infrared (NIR) or visible spectrum of 350 nm or greater. This is beneficial for diagnostic or therapeutic treatment of patients since visible and NIR light is less likely to damage tissue when utilized in biooptical diagnostic and therapeutic procedures. In contrast, ultraviolet (UV) light that has a wavelength of less than 350 nm can result in tissue damage. Longer wavelength light of 350 nm or greater is also able to penetrate more deeply into tissues thereby permitting either diagnostic or therapeutic procedures to be conducted in the tissues of interest that are not reached by UV wavelengths that are less than 350 nm. In one embodiment, the integrated photoactive analogs have absorption, excitation, and emission maximum wavelengths between about 400 nm and about 900 nm.

Two general approaches for integrating structural and functional moieties into a single molecular analog include, (a) transforming a known bioactive molecule into an integrated photoactive analog; and (b) transforming a photoactive entity into an integrated photoactive analog that is bioactive. In either approach, the resulting molecules possess the fundamental properties of photoactivity and biological function.

Depending on the structure and function, the integrated photoactive analogs of the present invention may be described as "integrated fluorophores," "integrated chromophores," "integrated photosensitizers," and the like. The general method for the design of integrated photoactive analogs principally involves: (a) selecting a desired bioactive molecule; (b) identifying the region of the molecule that contains replaceable moiety (e.g., aromatic and heteroaromatic); and (c) either replacing said moiety with a photoactive functional group of similar size, or modifying said moiety to make it photoactive. The resulting integrated photoactive analog of the present invention is useful for both diagnostic and therapeutic applications.

The synthesis and use of integrated photoactive analogs may be performed in a variety of ways. In one embodiment, a molecule with a known or desired structure and function is selected. For example, a selected photoactive molecule may target a specific tissue, cell, protein, receptor, and the like in a patient. A non-photoactive functional group within the molecular structure of the molecule is identified and replaced with a photoactive functional group to produce an integrated photoactive analog. The resulting integrated photoactive analog is administered to a patent in a diagnostically effective amount to detect the photoactive molecule within the patient. After a period of time has lapsed for the analog to bind to its target site, the whole body or a target tissue of a patient is exposed a light exhibiting a 350 to 1200 nm wavelength. In one example, the whole body or a target tissue of a patient is then exposed a light exhibiting a wavelength in the range of 400-900 nm. Light emanating from the patient as a result of the absorption and excitation of the integrated photoactive analog is then detected. By evaluating the location and strength of light emanating from the patient, a diagnosis may be made as a result of the targeting properties of the integrated photoactive analog.

The integrated photoactive analog can also be utilized to therapeutically treat a patient afflicted with a condition that exhibits a diseased tissue or cell that is targeted by the analog. In one embodiment, the analog targets an integrin receptor that is associated with a tissue or cell of interest. In another embodiment, the analogs are photoactive inhibitors that target tubulin assembly agents. In another embodiment the analogs are photoactive inhibitors that target vascular disruption agents. In still another embodiment, the analogs are photoactive inhibitors that target kinases, for example, $\beta$-RAF kinase.

After the integrated photoactive analog is administered to a patient, the analog targets and binds to the tissue, cell, protein, or receptor of interest. Light of an appropriate wavelength to photofragment/photoexcite the integrated photoactive analog into reactive species is administered to the patient in the area where the bound analog is located. The reactive species produced by the photofragmentation/photoexcitation of the integrated photoactive analog damages or kills diseased tissue or cells located in the proximity of the bound analog, thereby beneficially treating the patient's condition.

The development of an integrated photoactive analog involves selecting a suitable bioactive molecule that targets specific tissues, organs, lesions, cells, and the like. These include, but are not limited to, selective antagonists of various integrins such as $\alpha_{2b}\beta_{3a}$, $\alpha_v\beta_3$, $\alpha_5\beta_1$, and $\alpha_v\beta_5$ antagonists. The targeted integrins can be associated with a number of health conditions, such as angiogenesis, CV angiogenesis, restenosis, vascular disorders, osteoporosis, cancer, breast cancer, ovarian carcinoma, melanoma, tumors, thrombosis, inflammation, and the like, the diagnosis or therapeutic treatment of which is highly desirable.

Once a bioactive small molecule is selected, a non-photoactive moiety located on the molecule is identified and replaced with a photoactive moiety. Any moiety or portion of the molecule can be replaced by a photoactive moiety as long as the substitution does not result in substantial loss of biological activity or bioactive targeting properties of the resulting photoactive analog. For example, a non-photoactive moiety on a molecule that targets a specific tissue, receptor, etc. can be replaced with a photoactive moiety so long as the resulting photoactive analog also preferentially targets the specific tissue, cell, receptor, or the like.

Fragments and/or derivatives of small molecules that also target specific tissues, organs, receptors, etc. may also be modified or synthesized to produce photoactive molecules in accordance with the present invention. Photoactive analogs of fragments or derivatives of small molecules may likewise be used for diagnostic and phototherapeutic uses.

Non-limiting examples of photoactive moieties of the present invention include, but are not limited to olefins, benzenes, naphthalenes, naphthoquinones, fluorenes, anthracenes, anthraquinones, phenanthrenes, tetracenes, naphthacenediones, pyridines, quinolines, quinazine, quinoxalines, quinidine, pteridine, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, anthacylines; azulenes, and azaazulenes, indocyanines, benzoporphyrins, squaraines, corrins, coumarins, and cyanines. These photoactive moieties can be chemically converted into a biologically active photoactive small molecule (for example a receptor binding agent) by adding functional groups onto the photoactive moiety that cause the resulting small molecule to possess bioactivity or biological targeting properties.

The photoactive moieties of the present invention further include reactive species (or intermediates) useful in phototherapeutic procedures. Phototherapeutic moieties include, but are not limited to free radicals, carbenes, nitrenes, singlet oxygen, and the like. Examples of Type I photoreactive moieties that can be incorporated into a small molecule for the purpose of synthesizing a phototherapeutic analog include, but are not limited to, azides, azo compounds, diazo compounds, sulfenates, thiadiazoles, peroxides, and the free radical or reactive intermediate formed upon irradiation. Examples of Type II photoreactive moieties that can be incorporated into a small molecule for the purpose of synthesizing a phototherapeutic analog include, but are not limited to, phthalocyanines, porphyrins, extended porphyrins, and benzoporphyrins. This would be accomplished by chemically converting the phthalocyanine, porphyrin, extended porphyrin, and/or benzoporphyrin system to a biologically active substance (for example a receptor binding agent). This can be performed by adding functional groups onto the moiety that cause the resulting small molecule to possess bioactivity or biological targeting properties.

In one embodiment, a bioactive small molecule of the present invention comprises both a photoactive moiety and a photoreactive moiety.

Once an integrated photoactive analog has been created, it is administered to an individual. An appropriate amount of time is given for the analog to bind to the target tissue or cell, or the like in the patient. It will be understood that the administration of the compounds and compositions of the present invention is determined by the attending physician within the scope of sound medical judgment. The specific effective dose level for any particular patient depends upon a variety of factors including the disorder being treated, the severity of the disorder; activity of the specific compound employed; the specific composition employed, age, body weight, general health, sex, diet of the patient. The detection of the integrated photoactive analog is achieved by optical fluorescence, absorbance, or light scattering methods known in the art using invasive or non-invasive probes such as endoscopes, catheters, ear clips, hand bands, head bands, surface coils, finger probes, and the like (Muller et al.). The imaging can be achieved using planar imaging, optical tomographic, optical coherence tomographic, endoscopic, photoacoustic, sonofluorescent, confocal microscopic, or light scattering devices known in the art.

Similar to the diagnostic procedure described above, the integrated photoactive analog can be administered to an individual for therapeutic purposes. After administering the integrated photoactive analog to a patient, an appropriate amount of time is given for the analog to bind to the target tissue or cell, or the like in the patient. The patient may be optionally imaged as described above to determine the location where the analog is bound within the patient. Once the analog is determined to be bound to the targeted site or sites, the patient is irradiated with a wavelength and intensity of light sufficient to cause photofragmentation of the integrated photoactive analog. The photofragmentation typically results in homolytic cleavage of the analog, resulting in the generation of free radical intermediates. The generated free radicals then damage diseased tissues or cells of the targeted site(s) to which the integrated photoactive analog had bound, thereby therapeutically treating the condition of the patient.

In one embodiment, the non-photoactive moiety is an aromatic or heteroaromatic moiety located on the non-photoactive molecule that is replaced with a photoactive aromatic or heteroaromatic moiety. In another example, a non-photoactive aromatic or heteroaromatic moiety is replaced with an aromatic or heteroaromatic moiety having the same number of atoms in the ring structure as the non-photoactive moiety. In still another example, the non-photoactive aromatic or heteroaromatic moiety is replaced with a pyrazine, azulene, or azaazulene moiety.

In one embodiment, non-photoactive bioactive small molecules comprise a phenyl group within the molecule that comprises the structure:

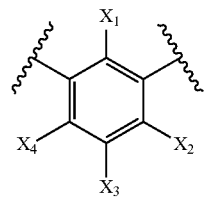

wherein $X_1$-$X_4$ are independently selected from the group consisting of hydrogen, hydroxyl, amino, C1-C6 alkyl, carboxyl, carbonyl, amido, ester, keto, nitro, aryl, heteroaryl, cyano, halogen, thiol, alkyl sulfide, aryl sulfide, heteroaryl sulfide, sulfone, sulfoxide, sulfonic acid, sulfonamide, phosphonate, olefin, alkyne, alkyl ether, aryl ether, heteroaryl ether.

The phenyl group of the non-photoactive bioactive small molecule is replaced with a photoactive pyrazine group that comprises the formula:

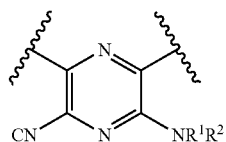

wherein $R_1$ and $R_2$ are independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl. In one example, $R_1$ and $R_2$ are each hydrogen.

In another embodiment, non-photoactive bioactive small molecules comprise a phenyl group within the molecule having a formula:

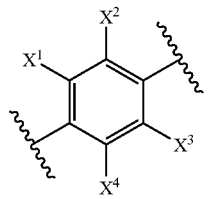

wherein $X^1$-$X^4$ are independently selected from the group consisting of carboxyl, carbonyl, amido, ester, keto, nitro, aryl, heteroaryl, cyano, halogen, thiol, alkyl sulfide, aryl sulfide, heteroaryl sulfide, sulfone, sulfoxide, sulfonic acid, sulfonamide, phosphonate, olefin, alkyne, alkyl ether, aryl ether, heteroaryl ether.

The phenyl group of the non-photoactive bioactive small molecule is replaced with a photoactive pyrazine group that comprises the formula:

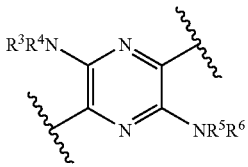

wherein $R^3$, $R^4$, $R^5$, and $R^6$ are independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl. In one example, $R^3$-$R^6$ are methyl groups.

In another embodiment, the photoactive group is a photoactive pyrazine group that comprises the formula:

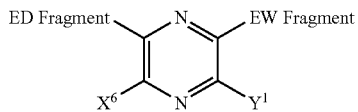

wherein EW Fragment is a necessary fragment of the small molecule that is attached to the pyrazine group by a substituent that is principally electron withdrawing and ED Fragment is a necessary fragment of the small molecule that is attached to the pyrazine group by a substituent that is principally electron donating; wherein a "necessary fragment" is a fragment of the small molecule that is necessary to achieve the desired bioactivity of the small molecule. $X^6$ is an electron withdrawing substituent and $Y^1$ is an electronic donating moiety. Examples of EW Fragments include, but are not limited to, fragments that are attached to the pyrazine group by a carboxylic acid derivative, a carbonyl group, a sulfoxy group, or a phosphonate group. Examples of ED Fragments include, but are not limited to, fragments that are attached to the pyrazine group by a nitrogen atom.

In one embodiment, the ED Fragment and/or the EW Fragment may be attached to the pyrazine group by a chemically unsaturated linking moiety conjugating an electron donating or electron withdrawing group to a carbon atom of the pyrazine ring by a resonance bond (i.e., π-extension). In general, conjugation (π-extension) of a chromophore or fluorophore to other unsaturated groups raises the energy level of the highest occupied molecular orbital (HOMO) and lowers the energy level of the lowest unoccupied molecular orbital (LUMO) of the molecule. As a result, less energy is required for an electronic transition in the conjugated π-system over the analogous non-conjugated pyrazine derivative. The more π-extending substituents that are attached to a pyrazine derivative, the less energy required for the electronic transition and therefore the longer the wavelength at which the transition occurs. By extending the absorption wavelengths, these pyrazine derivatives may also be used in the near infrared spectrum for imaging purposes. Typical unsaturated linking moieties include alkenyl, alkynyl, aryl, heteroaryl, anilino (-Ph-NH—), and azo (—NH=NH—) groups. Examples of linking groups include, but are not limited to, (a) alkenyls (e.g., 1-propenyl, 1-butenyl, 1-hexenyl, 2,4-hexadienyl); (b) alkynyls (e.g., 1-butynyl and 2,4-hexadiynyl); (c) aryls (e.g., phenyl, naphthyl, biphenyl, and anthracene); heteroaryls (e.g., pyridine, pyrimidine, pyrazine, triazine, pyridazine, tetrazine, furan, benzofuran, thiophene, imidazole, thiazole, thiadazole, oxazole, pyrrole, indole, triazole, and nucleic acid groups such as uracil, guanine, adenine, cytosine, and thymine); (d) anilino and polyanilino, and (e) azo. Examples of small molecules that comprise fragments which include an extended Π group are illustrated below in Compound 51 and Compound 59.

In one embodiment, the EW Fragment is a necessary fragment of the small molecule that is attached to the pyrazine group by a substituent selected from the group consisting of —CN, —$CO_2R^{31}$, —$CONR^{32}R^{33}$, —$COR^{34}$, —$NO_2$, —$SOR^{35}$, —$SO_2R^{36}$, —$SO_2OR^{37}$, —$PO_3R^{38}R^{39}$; the ED Fragment is a necessary fragment of the small molecule that is attached to the pyrazine group by a substituent selected from the group consisting of —$OR^{40}$, —$SR^{41}$, —$NR^{42}R^{43}$, —$N(R^{44})COR^{45}$, —$P(R^{46})_3$, —$P(OR^{47})_3$; $X^6$ is selected from the group consisting of —CN, —$CO_2R^{31}$, —$CONR^{32}R^{33}$, —$COR^{34}$, —$NO_2$, —$SOR^{35}$, —$SO_2R^{36}$, —$SO_2OR^{37}$, —$PO_3R^{38}R^{39}$; and $Y^1$ is selected from the group consisting of —$OR^{40}$, —$SR^{41}$, —$NR^{42}R^{43}$, —$N(R^{44})COR^{45}$, —$P(R^{46})_3$, —$P(OR^{47})_3$, and substituents corresponding to Formula A below. $Z^1$ may be a single bond, —$CR^{48}R^{49}$, —O, —$NR^{50}$, —$NCOR^{51}$, —S, —SO and —$SO_2$.

Formula A

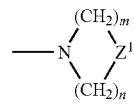

$R^{31}$ to $R^{51}$ may be any suitable substituent capable of providing and/or enhancing desired biological and/or physicochemical properties of the pyrazine derivative of the integrated photoactive analog. In one embodiment, $R^{31}$ to $R^{51}$ are independently selected from the group consisting of —H, —$(CH_2)_aOR^{52}$, —$CH_2(CHOH)_aR^{53}$, —$CH_2(CHOH)_a CO_2H$, —$(CHCO_2H)_aCO_2H$, —$(CH_2)_aNR^{54}R^{55}$, —CH[$(CH_2)_bNH_2$]$_aCO_2H$, —CH[$(CH_2)_bNH_2$]$_aCH_2OH$, —$CH_2(CHNH_2)_aCH_2NR^{58}R^{57}$, —$(CH_2CH_2O)_cR^{58}$, —$(CH_2)_dCO(CH_2CH_2O)_cR^{59}$, —$(CH_2)_aSO_3H$, —$(CH_2)_aSO_3^-$, —$(CH_2)_aOSO_3H$, —$(CH_2)_aOSO_3^-$, —$(CH_2)_aNHSO_3H$, —$(CH_2)_a NHSO_3^-$, —$(CH_2)_aPO_3H_2$, —$(CH_2)_aPO_3H^-$, —$(CH_2)_a PO_3^=$, —$(CH_2)_aOPO_3H_2$, —$(CH_2)_aOPO_3H^-$ and —$(CH_2)_a OPO_3$. In such embodiments, $R^{52}$ to $R^{59}$ are independently —H or —$CH_3$. In one group of embodiments, $R^{31}$ to $R^{51}$ are independently selected from the group consisting of —H, —$(CH_2)_aOR^{52}$, —$CH_2(CHOH)_aR^{53}$, —$CH_2(CHOH)_a CO_2H$, —$(CHCO_2H)_aCO_2H$, —$(CH_2)_aNR^{54}R^{55}$, —CH[$(CH_2)_bNH_2$]$_aCO_2H$, —CH[$(CH_2)_bNH_2$]$_aCH_2OH$, —$CH_2(CHNH_2)_aCH_2NR^{56}R^{57}$, —$(CH_2CH_2O)_cR^{58}$, —$(CH_2)_dCO(CH_2CH_2O)_cR^{59}$. In another group of embodiments, $R^{31}$ to $R^{51}$ are independently selected from the group consisting of —H, —$(CH_2)_aOR^{52}$, —$CH_2(CHOH)_aR^{53}$, —$(CH_2)_a NR^{54}R^{55}$, —$(CH_2CH_2O)_cR^{58}$, and —$(CH_2)_dCO(CH_2CH_2O)_dR^{59}$. In still another group of embodiments, $R^{31}$ to $R^{51}$ are independently selected from the group consisting of —H, —$(CH_2)_aOR^{52}$, —$CH_2(CHOH)_aR^{53}$, —$(CH_2)_a NR^{54}R^{55}$, and —$(CH_2)_dCO(CH_2CH_2O)_dR^{59}$.

In the above embodiments, 'a', 'b', and 'd' independently vary from 1 to 10, 'c' varies from 1 to 100, and 'm' and 'n' independently varies from 1 to 3. In some embodiments, each of 'a', 'b', and 'd' independently varies from 1 to 6. In some embodiments, 'c' varies from 1 to 20. In some embodiments, 'm' and 'n' are independently 0 or 1.

Once an integrated photoactive analog has been created, the analog is administered to an individual. An appropriate amount of time is given for the analog to bind to the target tissue, cell, protein, receptor, and the like. in the patient. It will be understood that the administration of the compounds and compositions of the present invention is determined by the attending physician within the scope of sound medical judgment. The specific effective dose level for any particular patient depends upon a variety of factors including the disorder being treated, the severity of the disorder; activity of the specific compound employed; the specific composition employed, age, body weight, general health, sex, diet of the patient. The detection of the integrated photoactive analog is achieved by optical fluorescence, absorbance, or light scattering methods known in the art using invasive or non-invasive probes such as endoscopes, catheters, ear clips, hand bands, head bands, surface coils, finger probes, and the like (Muller et al.). The imaging can be achieved using planar imaging, optical tomographic, optical coherence tomographic, endoscopic, photoacoustic, sonofluorescent, confocal microscopic, or light scattering devices known in the art.

Similar to the diagnostic procedure described above, the integrated photoactive analog can be administered to an individual for therapeutic purposes. After administering the integrated photoactive analog to a patient, an appropriate amount of time is given for the analog to bind to the target tissue, cell, protein, receptor, and the like. in the patient. The patient may be optionally imaged as described above to determine the location where the analog is bound within the patient. Once the analog is determined to be bound to the targeted site or sites, the patient is irradiated with a wavelength and intensity of light sufficient to cause photofragmentation of the integrated photoactive analog. The photofragmentation typically results in homolytic cleavage of the analog, resulting in the generation of free radical intermediates. The generated free radicals then damages tissue or cells in the proximity of the targeted site to which the integrated photoactive analog had bound, thereby therapeutically treating the condition of the patient.

In one embodiment, the non-photoactive small molecule is an $\alpha_v\beta_3$ antagonist that comprises a non-photoactive phenyl group. The non-photoactive small molecule is represented by Formula 1:

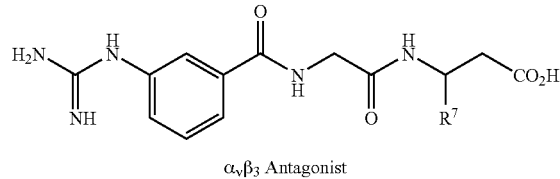

$\alpha_v\beta_3$ Antagonist

Formula 1

$R_7$ is selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl, aryl, and heteroaryl.

The non-photoactive phenyl group of Formula 1 is replaced with a pyrazino moiety, forming an integrated photoactive analog of the $\alpha_v\beta_3$, $\alpha_5\beta_1$, and $\alpha_v\beta_5$ antagonist that is represented by Formula 2:

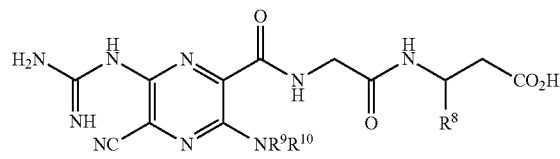

Integrated $\alpha_v\beta_3$ Photoactive Drug

Formula 2

The resulting integrated photoactive analog comprises moieties $R^8$ to $R^{10}$ independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl. The synthesis of the integrated photoactive drug of Formula 2 is accomplished by known methods in the art. A non-limiting example of one method is outlined in FIG. 1.

Figure 1B:
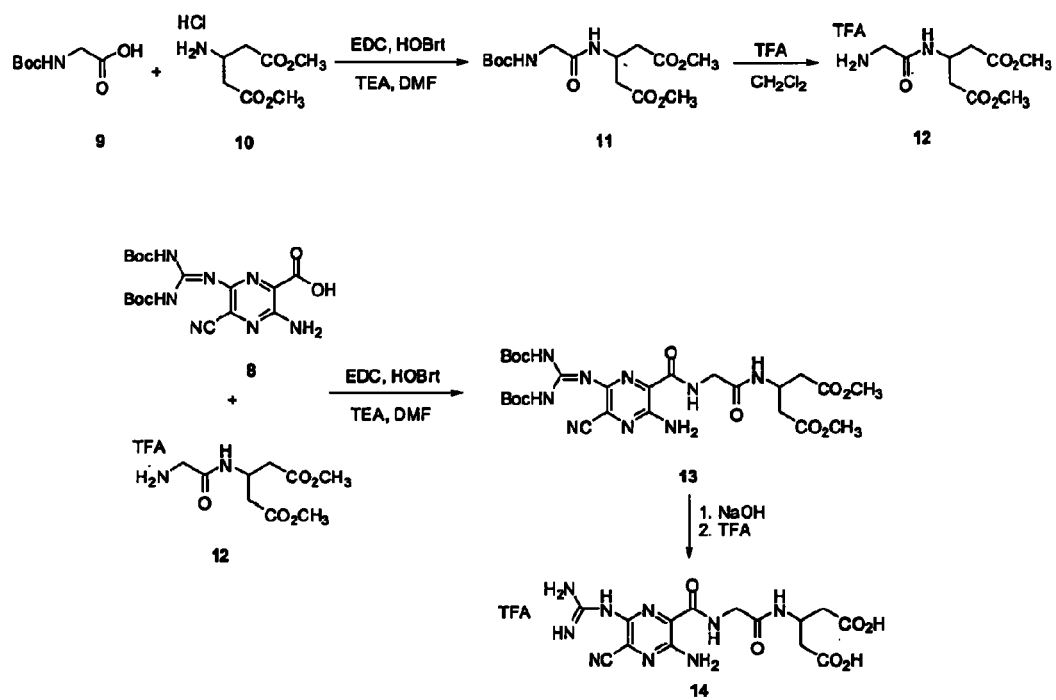

In one embodiment, the integrated photoactive analog is an $\alpha_v\beta_3$, $\alpha_5\beta_1$, and $\alpha_v\beta_5$ antagonist that is represented by Formula 14, the synthesis of which is outlined in FIGS. 1A and 1B:

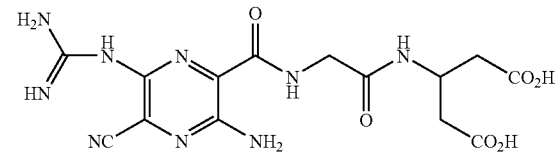

Compound 14

Figure 2:
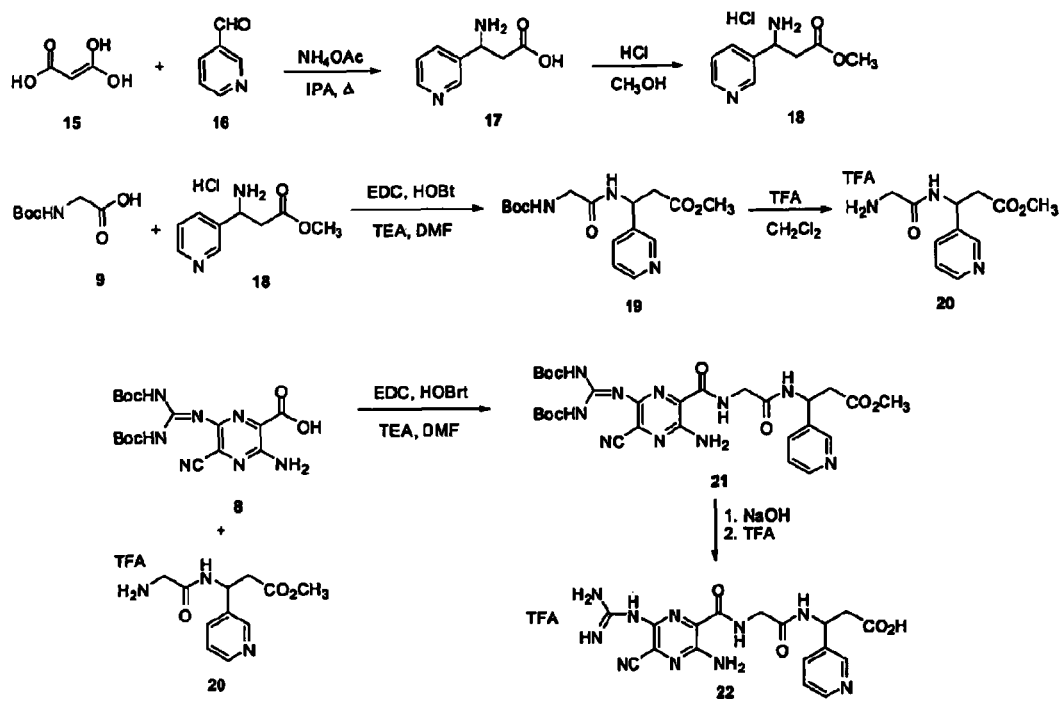
FIG. 2. Synthesis of Integrated Photoactive $\alpha_v\beta_3$ Antagonist Compound 22.

In another embodiment, the integrated photoactive analog is an $\alpha_v\beta_3$, $\alpha_5\beta_1$, and $\alpha_v\beta_{5\ 3}$ antagonist that is represented by Compound 22, the synthesis of which is outlined in FIG. 2:

Compound 22

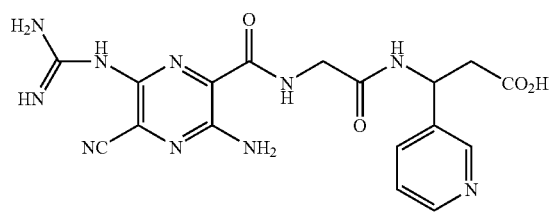

Figure 3:
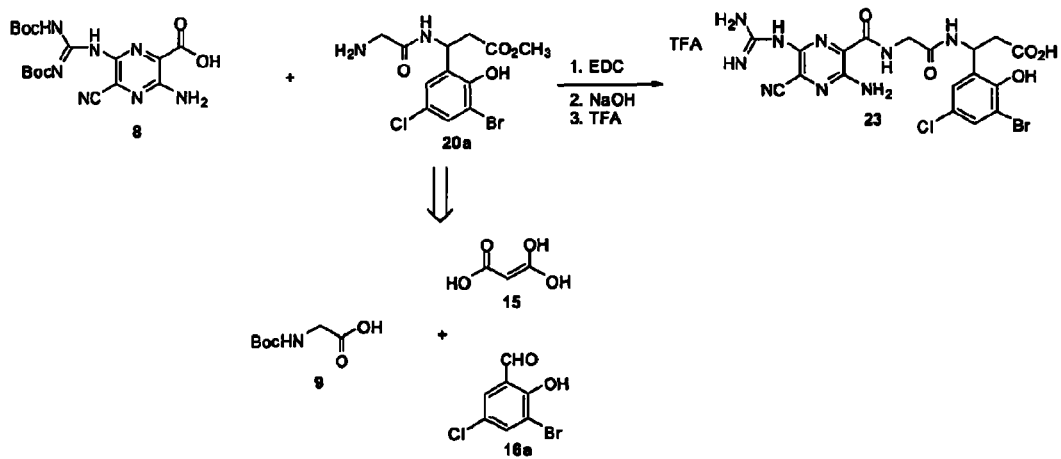
FIG. 3. Synthesis of Integrated Photoactive $\alpha_v\beta_3$ Antagonist Compound 23.

In another embodiment, the integrated photoactive analog is an $\alpha_v\beta_3$, $\alpha_5\beta_1$, and $\alpha_v\beta_5$ antagonist that is represented by Compound 23, the synthesis of which is outlined in FIG. 3:

Compound 23

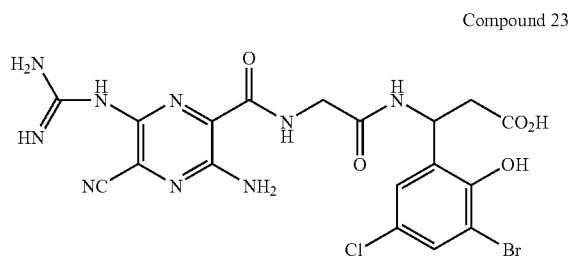

Figure 4:
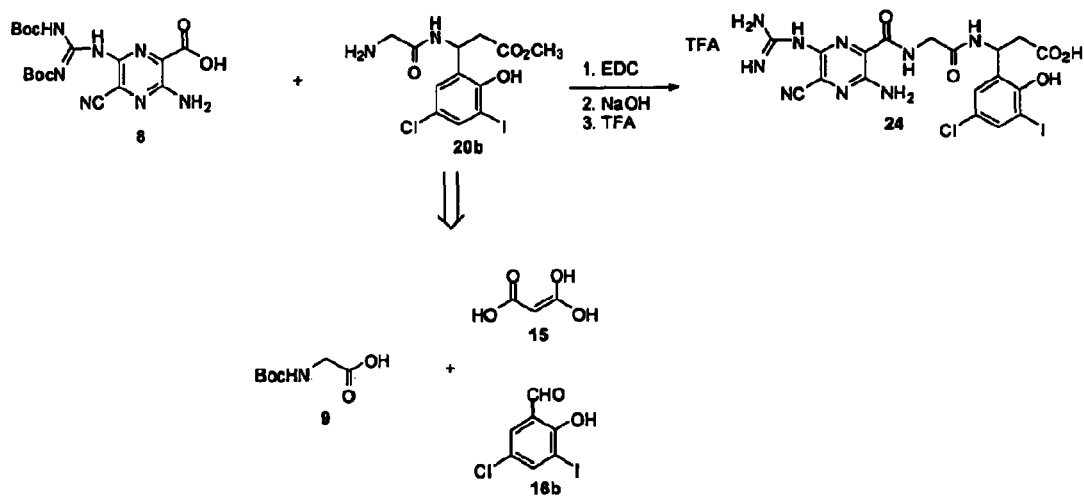
FIG. 4. Synthesis of Integrated Photoactive $\alpha_v\beta_3$ Antagonist Compound 24.

In another embodiment, the integrated photoactive analog is an $\alpha_v\beta_3$, $\alpha_5\beta_1$, and $\alpha_v\beta_5$ antagonist that is represented by Compound 24, the synthesis of which is outlined in FIG. 4:

Compound 24

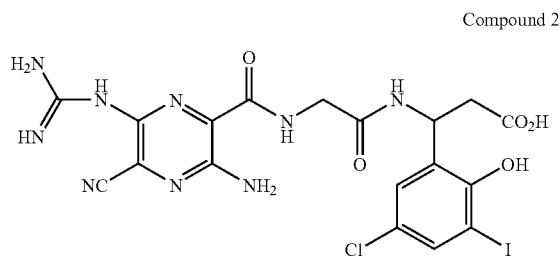

Figure 5A:
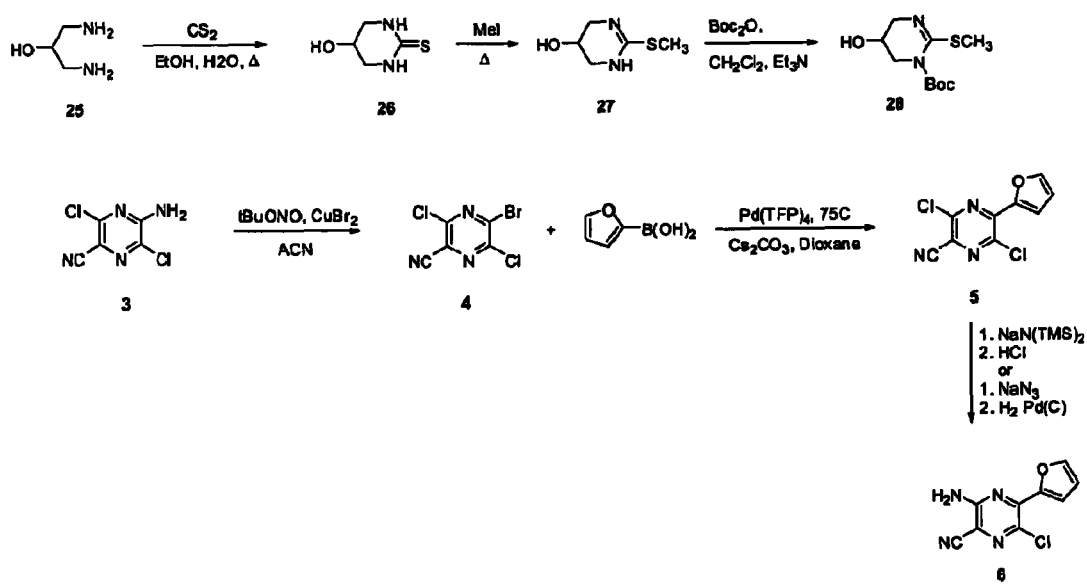
FIGS. 5A and 5B. Synthesis of Integrated Photoactive $\alpha_v\beta_3$ Antagonist Compound 32.
Figure 5B:
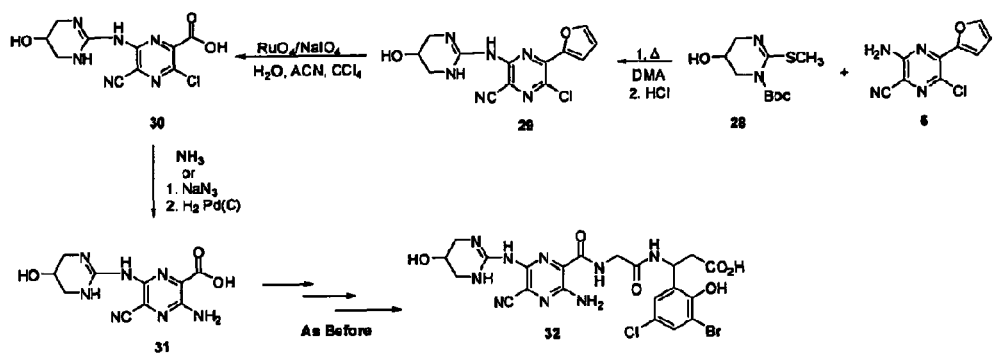

In another embodiment, the integrated photoactive analog is an $\alpha_v\beta_3$, $\alpha_5\beta_1$, and $\alpha_v\beta_5$ antagonist that is represented by Compound 32, the synthesis of which is outlined in FIGS. 5A and 5B:

Compound 32

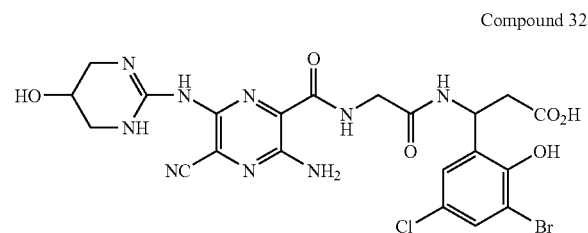

Figure 6:
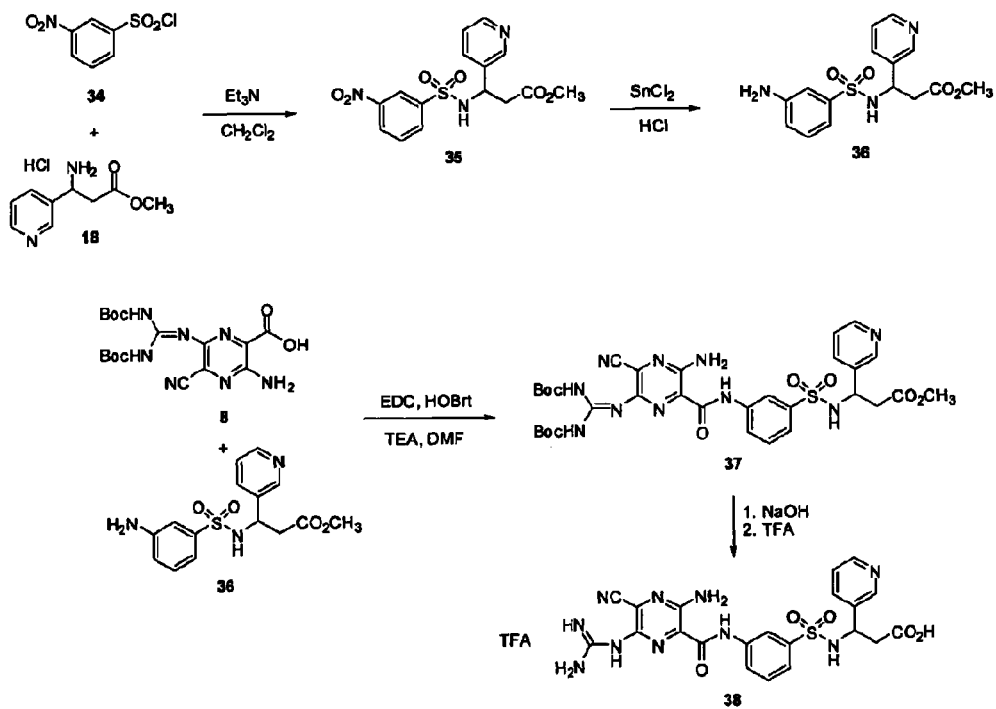
FIG. 6. Synthesis of Integrated Photoactive $\alpha_v\beta_3$ Antagonist Compound 38.

In another embodiment, the integrated photoactive analog is an $\alpha_v\beta_3$, $\alpha_5\beta_1$, and $\alpha_v\beta_5$ antagonist that is represented by Compound 38, the synthesis of which is outlined in FIG. 6:

Compound 38

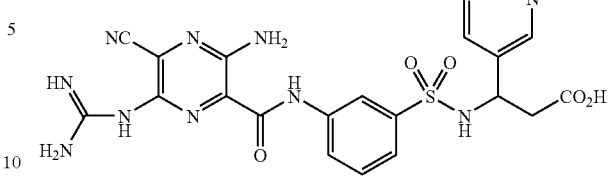

Figure 7:
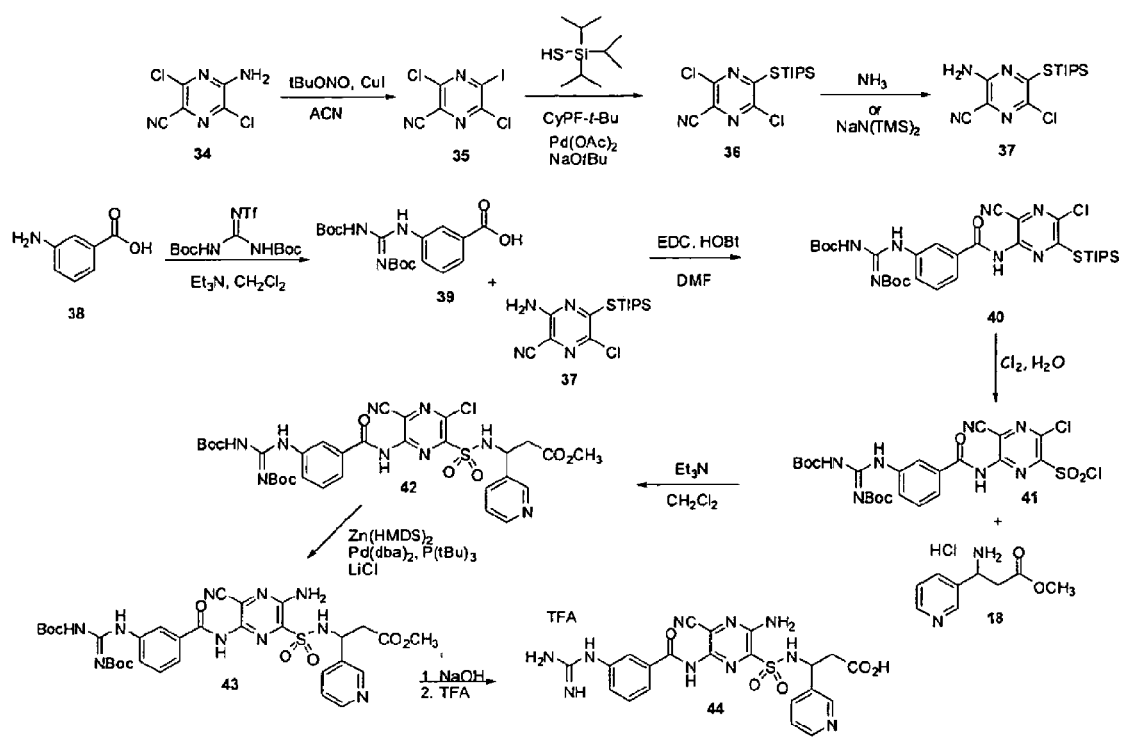
FIG. 7. Synthesis of Integrated Photoactive $\alpha_v\beta_{3a}$ Antagonist Compound 44.

In another embodiment, the integrated photoactive analog is an $\alpha_v\beta_3$, $\alpha_5\beta_1$, and $\alpha_v\beta_5$ antagonist that is represented by Compound 44, the synthesis of which is outlined in FIG. 7:

Compound 44

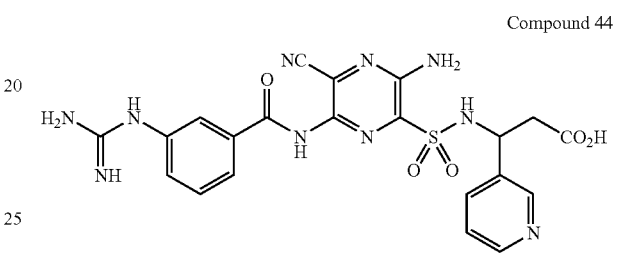

In another embodiment, the integrated photoactive analog is an analog of an $\alpha_v\beta_3$, $\alpha_5\beta_1$, and $\alpha_v\beta_5$ antagonist which is a photosensitizer having the structural Formula 3:

Formula 3

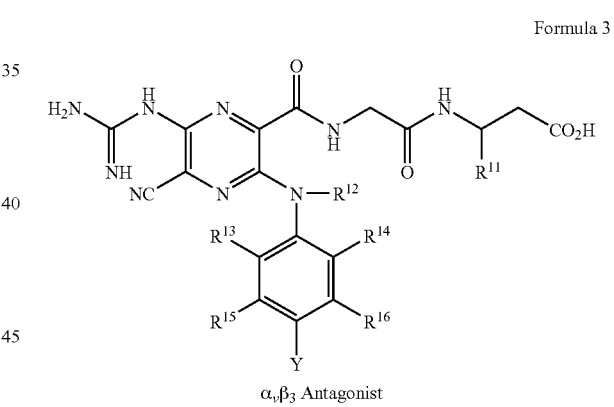

$\alpha_v\beta_3$ Antagonist wherein $R^{11}$ and $R^{12}$ are independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl, aryl, and heteroaryl; Y is —$N_3$ or —SOAr; $R^{13}$ to $R^{16}$ are independently selected from the group consisting of hydrogen, C1-C6 alkyl, C1-C6 acyl, C1-C6 alkoxycarbonyl, halogen, —CN, —$NO_2$, and —$NR^{17}R^{18}$; and $R^{17}$ and $R^{18}$ are independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl, aryl, and heteroaryl.

In one example, $R^{11}$ and $R^{12}$ are independently hydrogen and C1-C6 alkyl; Y is —$N_3$ or —SOAr; $R^{13}$ to $R^{16}$ are independently selected from the group consisting of hydrogen, C1-C6 alkoxycarbonyl, —F, —CN, —$NO_2$, and —$NR^{17}R^{18}$; and $R^{17}$ and $R^{18}$ are independently hydrogen and C1-C6 alkyl.

In another example, the non-photoactive phenyl group of Formula 3 is replaced with a photoactive pyrazino group to form the integrated photoactive analog of Formula 4:

Formula 4 wherein $R^{19}$ and $R^{20}$ are selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl. The synthesis of the integrated photoactive drug of Formula 4 is accomplished by known methods in the art. A non-limiting example of one method is outlined in FIGS. 1A and 1B.

In another embodiment, the integrated photoactive analog is an analog of an $\alpha_v\beta_3$ antagonist comprising a photoactive pyrazino group wherein photoreactive moieties are attached to a pendant phenyl group to form the integrated photoactive/phototherapeutic analog of Formula 5:

Formula 5 wherein $R^{19}$ and $R^{20}$ are selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl, aryl, and heteroaryl; and $R^{21}$-$R^{24}$ are independently selected from the group consisting of hydrogen; azide, azo, diazo, sulfenate, thiadiazole, peroxide, and the free radical or reactive intermediate formed upon irradiation;

In another embodiment, a non-photoactive small molecule drug is Xemilofiban, an $\alpha_{2b}\beta_{3a}$ antagonist having the structural Formula 6:

Formula 6

Xemilofiban ($\alpha_{2b}\beta_{3a}$ Antagonist)

The non-photoactive phenyl group of Xemilofiban is replaced with a pyrazino moiety, forming an integrated photoactive analog of the $\alpha_{2b}\beta_{3a}$ antagonist that is represented by Formula 7:

Formula 7

Integrated $\alpha_{2b}\beta_{3a}$ Photoactive Drug wherein $R^{25}$ to $R^{28}$ are independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl. The synthesis of the integrated photoactive drug of Formula 6 is accomplished by known methods in the art. A non-limiting example of one method is outlined in FIG. 2.

In another embodiment, the non-photoactive pyrazine group of Xemilofiban (Formula 5) is replaced with a pyrazino moiety to form the photoactive $\alpha_{2b}\beta_{3a}$ antagonist having the structure represented by Formula 8:

Formula 8

Integrated $\alpha_{2b}\beta_{3a}$ Phototherapeutic wherein $R^{29}$ and $R^{30}$ are independently selected from the group consisting of hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, and C1-C6 aminoalkyl; and $X^5$ is a substituent comprising a Type I photoreactive group attached to an electronic donating group. Examples of Type I photoreactive groups include, but are not limited to, azides, azo compounds, diazo compounds, sulfenates, thiadiazoles, peroxides, and the free radical or reactive intermediate forming groups thereof. Examples of electronic donating groups include, but are not limited to amine groups, phenyl amine substituents, and the like. In one example, $X^5$ is a Type I photoreactive group attached to a phenyl amine substituent. In another example, $X^5$ is selected from the group consisting of Type I azidophenyl amine substituents. The synthesis of the integrated photoactive drug of Formula 6 is accomplished by known methods in the art. A non-limiting example of one method is outlined in FIG. 3.

Figure 8:
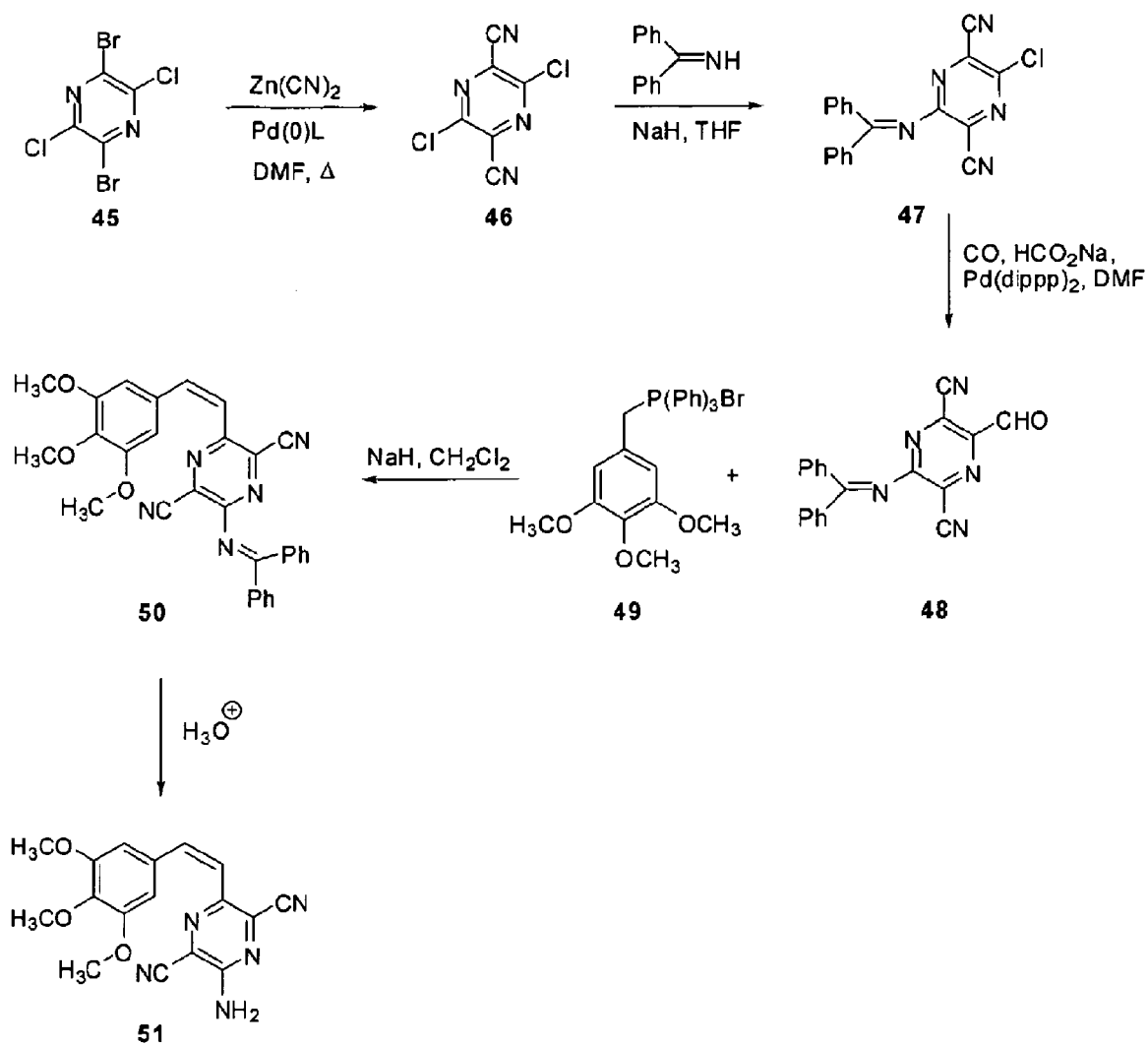
FIG. 8. Synthesis of Integrated Photoactive Inhibitor of tubulin assembly, Compound 51.

In another embodiment, the integrated photoactive analog is an inhibitor of tubulin assembly and vascular disruption agents that is represented by Compound 51, the synthesis of which is outlined in FIG. 8:

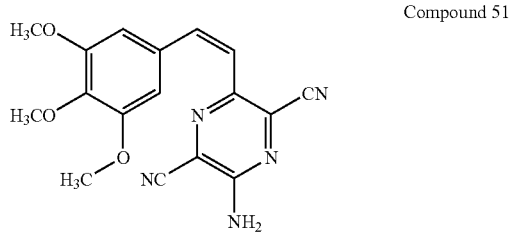

Compound 51

Figure 9:
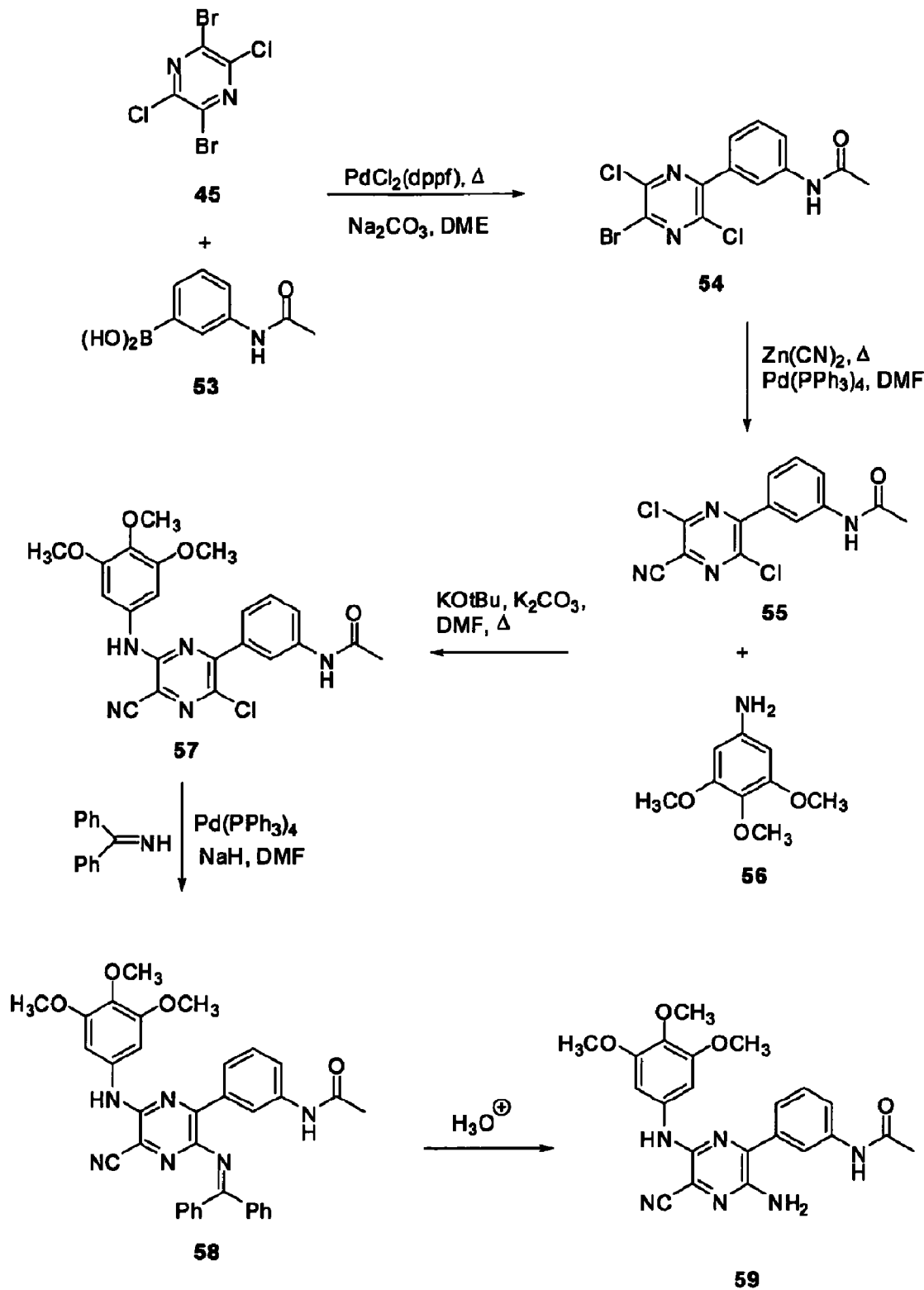
FIG. 9. Synthesis of Integrated Photoactive Inhibitor of $\beta$-RAF kinase, Compound 59.

In another embodiment, the integrated photoactive analog is an inhibitor of β-RAF kinase that is represented by Compound 59, the synthesis of which is outlined in FIG. 9:

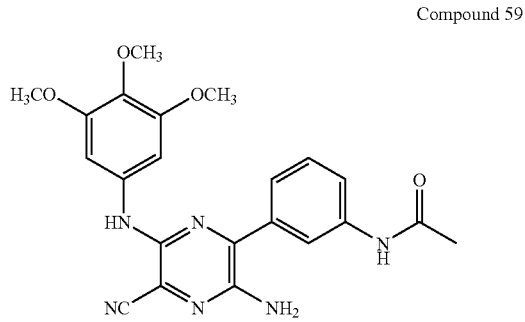

Compound 59

Formulation

The integrated photoactive agents of the present invention can be formulated for enteral (oral or rectal), parenteral, topical, transdermal, or subcutaneous administration. Topical, transdermal, and cutaneous delivery can also include aerosols, creams, gels, emulsions, solutions, or suspensions. Delivery into and through the skin can be enhanced in accordance with known methods and agents such as transdermal permeation enhancers, for example, "azone", N-alkylcyclic amides, dimethylsulfoxide, long-chained aliphatic acids ($C_{10}$), etc. (Gennaro).

The method for preparing pharmaceutically acceptable formulations can be accomplished according to methods known in the art (Gennaro). A formulation is prepared using any of the integrated photoactive agents, along with pharmaceutically acceptable buffers, surfactants, excipients, thixotropic agents, flavoring agents, stabilizing agents, or skin penetration enhancing agents. If the inventive compound is water soluble, a solution in physiological saline may be administered. If the compound is not water soluble, the compound can be dissolved in a biocompatible oil (e.g., soybean oil, fish oil, vitamin E, linseed oil, vegetable oil, glyceride esters, long-chained fatty esters, etc.) and emulsified in water containing surface-active compounds (e.g., vegetable or animal phospholipids; lecithin; long-chained fatty salts and alcohols; polyethylene glycol esters and ethers; etc.), and administered as a topical cream, suspension, water/oil emulsion, or water/oil microemulsion.

The integrated photoactive agents may also be encapsulated into micelles, liposomes, nanoparticles, shell cross-linked nanoparticles, dendrimers, dendrons, microcapsules, or other organized microparticles, and administered by any of the routes described previously. The integrated photoactive agents may also be chemically conjugated to nanoparticles, shell cross-linked nanoparticles, dendrimers or dendrons for the purpose of simultaneously effecting an integrated photonic effect and a multivalent biological effect. These formulations may enhance stability of said agents in vivo. Encapsulation methods include detergent dialysis, freeze drying, film forming, or injection (Janoff et al.). The method of making liposomes and encapsulating various molecules within them are well known in the art (Braun-Falco et al. and Lasic et al.).

Dosage

The compositions comprising the integrated photoactive analogs of the present invention may be administered in a single dose or in many doses to achieve the effective diagnostic or therapeutic objective. After administration, the integrated photoactive analog accumulates at a target tissue, and the selected target site is exposed to light with a sufficient power and intensity to render a diagnosis and/or treatment. Such doses may vary widely depending upon the particular integrated photoactive analog employed, the organs or tissues to be examined, the equipment employed in the clinical procedure, the efficacy of the treatment achieved, and the like. The dose of the compound may vary from about 0.1 mg/kg body weight to about 500 mg/kg body weight, typically from about 0.5 to about 2 mg/kg body weight. For parenteral administration, a sterile solution or suspension comprises the integrated photoactive agent in a concentration range from about 1 nM to about 0.5 M. In another example, the sterile solution or suspension comprises the integrated photoactive agent in a concentration range from about 1 μM to about 10 mM.

Although the present invention can be beneficially utilized in the form of small molecules, the methodology is also applicable to any bioactive molecule, large or small. The present invention is useful for various biomedical optics applications including, but are not limited to, planar imaging, optical tomography, optical coherence tomography, endoscopy, photoacoustic technology, sonofluorescence technology, light scattering technology, laser assisted guided surgery (LAGS), confocal microscopy, dynamic organ function monitoring, and phototherapy.

ABBREVIATIONS AND DEFINITIONS

To facilitate understanding of the invention, a number of terms are defined below:

"Bioactive small molecule" refers to a molecule whose molecular weight is generally less than 1000 Daltons and binds to a particular biological target such as receptors, enzymes, and the like.

"Diagnostically effective amount" is meant an amount of the substance in question which will, in a majority of patients, be an adequate quantity of substance to be able to detect the targeted tissue of cells if present in the patient to whom it is administered. The term "an effective amount" also implies that the substance is given in an amount which only causes mild or no adverse effects in the subject to whom it has been administered, or that the adverse effects may be tolerated from a medical and pharmaceutical point of view in the light of the severity of the disease for which the substance has been given.

"Integrated non-photoactive functional group" refers to a functional group within a bioactive molecule that does not exhibit a peak excitation and emission peak in the range of 350-1200 nm.

"Photoactive functional units" or "photoactive moieties" refers to any functional group or moiety exhibiting an absorption, excitation, and emission maxima in the wavelength range of 350-1200 nm. Such functional groups or moieties include, but are not limited to, fluorophores, chromophores, photosensitizers, and photoreactive moieties, wherein "fluorophores," "chromophores," "photosensitizers," and "photoreactive" moieties have meanings that are commonly understood in the art.

"Photoreactive moiety" refers to a moiety of a molecule, which, when excited with light of wavelength 350 to 1200 nm, undergoes photochemical reaction to generate reactive species capable of causing tissue damage."

"Therapeutically-effective amount" refers to the amount of each agent that will achieve the goal of improvement in pathological condition severity and the frequency of incidence over treatment of each agent by itself, while avoiding adverse side effects typically associated with alternative therapies.

"Treatment" refers to any process, action, application, therapy, or the like, wherein a subject, including a human being, is provided medical aid with the object of improving the subject's condition, directly or indirectly, or slowing the progression of a pathological condition in the subject.

When introducing elements of the present invention or the embodiment(s) thereof, the articles "a", "an", and "the" are intended to mean that there are one or more of the elements. The terms "comprising", "including" and "having" are intended to be inclusive and mean that there may be additional elements other than the listed elements.

The following example illustrates specific embodiments of the invention. As would be apparent to skilled artisans, various changes and modifications are possible and are contemplated within the scope of the invention described.

Example 1

Preparation of 3,6-diamino-N2,N5-bis(4-carbamimidoylbenzyl)pyrazine-2,5-dicarboxamide

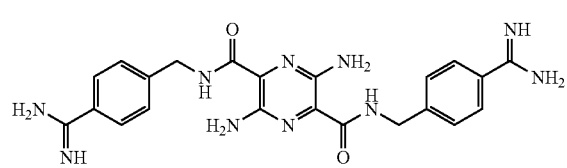

A mixture of 3,6-diaminopyrazine-2,5-dicarboxylic acid (250 mg, 1.40 mmol), 4-(aminomethyl)-benzamidine dihydrochloride (619 mg, 2.80 mmol), HOBt-H$_2$O (628 mg, 4.10 mmol), EDC-HCl (790 mg, 4.10 mmol) and triethylamine (2 mL) were stirred together in DMF (20 mL) for 16 h at room temperature. The mixture was concentrated to dryness and purified by medium pressure reversed phase chromagraphy (LiChroprep RP-18 Lobar (B) 25×310 mm—EMD chemicals 40-63 □m, ~70 g, 90/10 to 80/20 0.1% TFA-ACN) to afford 171 mg (27% yield) of example 1 as an orange foam: LCMS (5-95% gradient acetonitrile in 0.1% TFA over 10 min), single peak retention time=4.69 min on 250 C18 mm column, (M+H)$^+$=461. UV/vis (100 μM in PBS) $\lambda_{abs}$=437 nm. Fluorescence (100 nM) $\lambda_{ex}$=428 nm, $\lambda_{em}$=554 nm.

Examples 2-11 illustrate photoactive pyrazine groups that exhibit absorption, excitation, and emission maximum wavelengths that in the near-infrared (NIR) or visible spectrum of 350 nm or greater.

Example 2

Photoactivity of 3,6-diamino-N$^2$,N$^2$,N$^5$,N$^5$-tetrakis(2-methoxyethyl)pyrazine-2,5-dicarboxamide

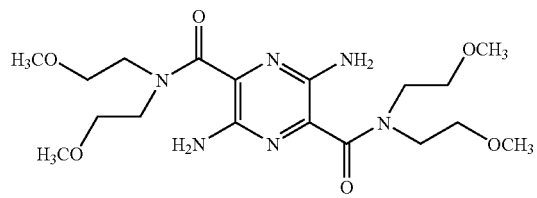

UV/vis (100 μM in PBS) $\lambda_{abs}$=394 nm. Fluorescence (100 nm) $\lambda_{ex}$=394 nm, $\lambda_{em}$=550 nm.

Example 3

Photoactivity of 3,6-diamino-N$^2$,N$^5$-bis(2,3-dihydroxypropyl)pyrazine-2,5-dicarboxamide

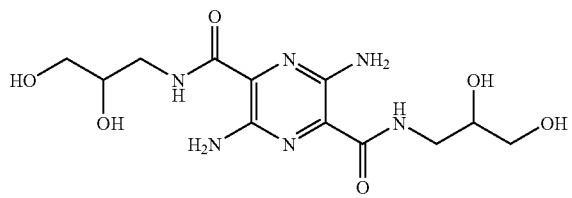

UV/vis (100 μM in PBS) $\lambda_{abs}$=434 nm. Fluorescence $\lambda_{ex}$=449 nm, $\lambda_{em}$=559 nm.

Example 4

Photoactivity of 3,6-Diamino-N$^2$,N$^5$-bis(serine)-pyrazine-2,5-dicarboxamide

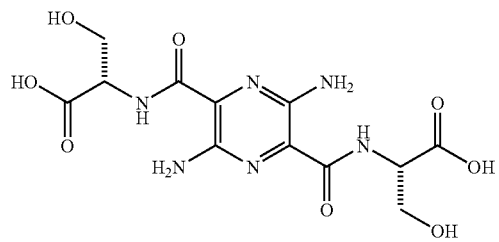

UV/vis (100 μM in PBS) $\lambda_{abs}$=432 nm. Fluorescence $\lambda_{ex}$=432 nm, $\lambda_{em}$=558 nm.

Example 5

Photoactivity of 3,6-bis(bis(2-methoxyethyl)amino)-$N^2,N^2,N^5,N^5$-tetrakis(2-methoxyethyl) pyrazine-2,5-dicarboxamide bis TFA salt

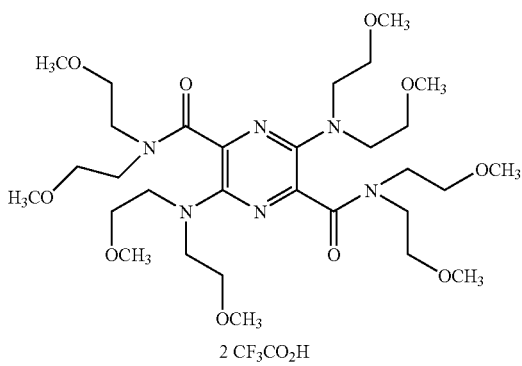

UV/vis (100 μM in PBS) $\lambda_{abs}$=434 nm. Fluorescence $\lambda_{ex}$=449 nm, $\lambda_{em}$=559 nm.

Example 6

Photoactivity of 3,6-diamino-$N^2,N^5$-bis(2-aminoethyl)pyrazine-2,5-dicarboxamide bis TFA salt

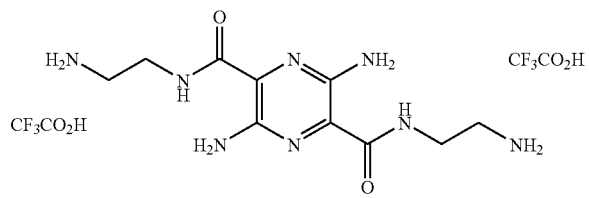

UV/vis (100 μM in PBS) $\lambda_{abs}$=435 nm. Fluorescence (100 nM) $\lambda_{ex}$=449 nm, $\lambda_{em}$=562 nm.

Example 7

Photoactivity of 3,6-Diamino-$N^2,N^5$-bis(D-Aspartate)-pyrazine-2,5-dicarboxamide

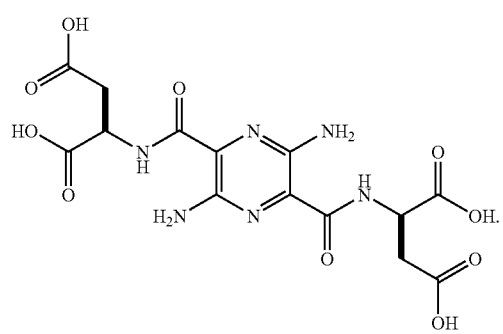

UV/vis (100 μM in PBS) $\lambda_{abs}$=433 nm. Fluorescence (100 nM) $\lambda_{ex}$=449 nm, $\lambda_{em}$=558 nm.

Example 8

Photoactivity of 3,6-Diamino-$N^2,N^5$-bis(14-oxo-2,5,8,11-tetraoxa-15-azaheptadecan-17-yl)pyrazine-2,5-dicarboxamide

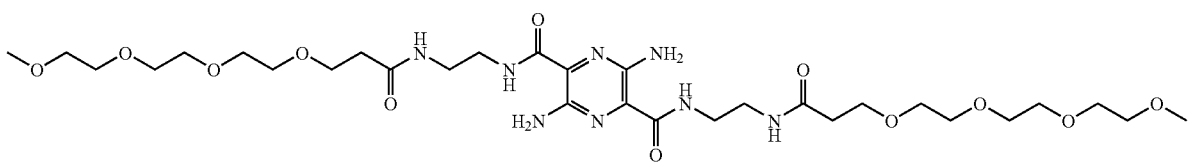

UV/vis (100 μM in PBS) $\lambda_{abs}$=437 nm. Fluorescence (100 nM) $\lambda_{ex}$=437 nm, $\lambda_{em}$=559 nm.

Example 9

Photoactivity of 3,6-Diamino-N²,N⁵-bis(26-oxo-2,5,8,11,14,17,20,23-octaoxa-27-azanonacosan-29-yl)pyrazine-2,5-dicarboxamide

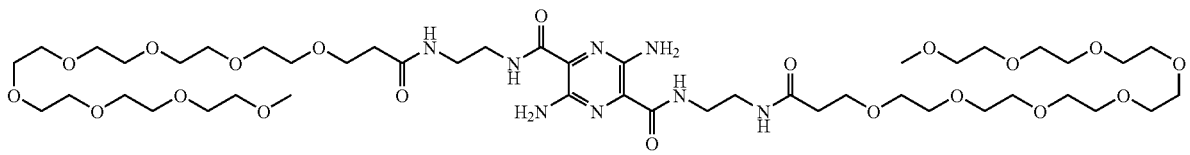

UV/vis (100 µM in PBS) $\lambda_{abs}$=438 nm. Fluorescence (100 nM) $\lambda_{ex}$=438 nm, $\lambda_{em}$=560 nm.

Example 10

Photoactivity of 3,6-Diamino-N²,N⁵-bis(38-oxo-2,5,8,11,14,17,20,23,26,29,32,35-dodecaoxa-39-azahentetracontan-41-yl)pyrazine-2,5-dicarboxamide

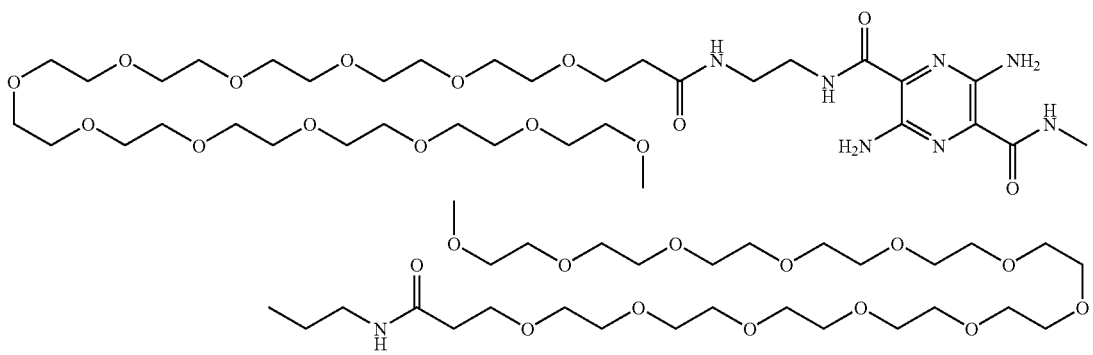

UV/vis (100 µM in PBS) $\lambda_{abs}$=449 nm. Fluorescence (100 nM) $\lambda_{ex}$=449 nm, $\lambda_{em}$=559 nm.

Example 11

Photoactivity of (R)-2-(6-(bis(2-methoxyethyl)amino)-5-cyano-3-morpholinopyrazine-2-carboxamido)succinic acid

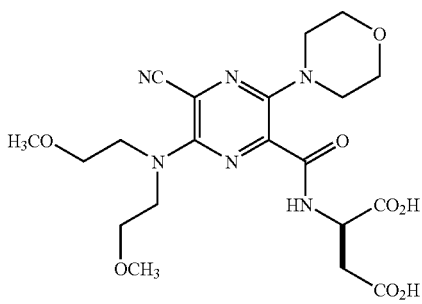

UV/vis (100 µM in PBS) $\lambda_{abs}$=438 nm. Fluorescence (100 nM) $\lambda_{ex}$=449 nm, $\lambda_{em}$=570 nm.

REFERENCES

Hassan, M.; Klaunberg, B. A. Biomedical applications of fluorescence imaging in vivo. *Comparative Medicine* 2004, 54(6), 635-644.

Licha, K.; Olbrich, C. Optical imaging in drug discovery and diagnostic applications. *Advances in Drug Delivery Reviews* 2005, 57(8), 1087-1108.

Shah, K.; Weissleder, R. Molecular optical imaging: applications leading to the development of present day therapeutics. *NeuroRx* 2005, 2(2), 215-225.

Vasquez, M. E. et al. 6-N,N-Dimethylamino-2,3-naphthalamide: A new environment-sensitive fluorescent probes in δ- and µ-selective opioid peptides. *Journal of Medicinal Chemistry* 2006, 49, 3653-3658.

Solban N.; Ortel, B.; Pogue, B.; Hasan, T. Targeted optical imaging and photodynamic therapy. *Ernst Schering Research Foundation Workshop* 2005, 49, 229-258.

Jain, R. K. Barriers to Drug Delivery in Solid Tumors. *Scientific American* 1994, 271, 58-65.

Hunter, D. H., and Luyt L. G. Single isomer technetium-99m tamoxifen conjugates. *Bioconjugate Chemistry* 2000, 11, 175-181.

Rajagopalan, R. Nitrogen sulfur ligands as opiate receptor drug mimics. U.S. Patent 1994: U.S. Pat. No. 5,330,737.

Rajagopalan, R. Metal containing steroid mimics and ligands useful in the preparation thereof. U.S. Patent 1997: U.S. Pat. No. 5,602,236.

Hom, R. K.; Katzenellenbogen, J. A. Synthesis of oxorhenium(V) complex mimic of a steroidal estrogen. *J. Org. Chem.* 1997, 62, 6290-6297.

Skaddan, M. B.; Katzenellenbogen, J. A. Integrated oxorhenium(V) complexes as estrogen mimics. *Bioconjugate. Chem.* 1999, 10, 119-129.

Miyata, K., et al. Synthesis and properties of a new fluorescent bicyclic 4-N-carbamoyl-deoxycytidine derivative. *Organic Letters* 2008, 8(8), 1545-1548.

Muller et al. Eds, *Medical Optical Tomography, SPIE* Volume IS11, 1993.

Waldman, S. ST receptor binding compounds and methods of using the same U.S. Patent 1996: U.S. Pat. No. 5,518,888.

Edelberg, J., Ballard, V. Restoring vascular Function. U.S. Publication No. 20060172943; PCT WO2005009366.

Schneider, H. et al. A novel peptide, PLAEIDGIELTY, for the targeting of $\alpha_\nu\beta_1$-integrins. *FESB Letters* 1998, 429(3), 269-273.

Nothnick, W. B. Therapeutic Targets for the Treatment of Endometriosis, *Expert Opinion* 2004, 8(5), 459-471.

Mayo, K. et al. Partial peptide mimetics and methods. PCT WO 03/070751; US Publication No. 20040053828.

Jaalouk, D. et al. Compositions and methods that related peptides that bind selectively to leukemia cells. PCT WO 2006010070. US Patent Application 2004, No. 586814.

A. R. Gennaro (Ed.). Remington: *The Science and Practice of Pharmacy*, 20th Edition. Lippincott Williams & Wilkins: Baltimore, 2000.

Janoff, A. S. et al. Methods of preparing low-toxicity drug-lipid complexes. U.S. Patent 2002: U.S. Pat. No. 6,406,713.

Braun-Falco et al. (Eds.). *Liposome Dermatics*. Griesbach Conference, Springer-Verlag: Berlin, 1992.

Lasic and Martin (Eds.). *Stealth Liposomes*. CRC Press: London, 1995.

Wentroup, C. et al. Synthesis of 1-azaazulene and benz[a]azulene by carbene rearrangement. *J. Am. Chem. Soc.* 1984, 106(12), 3705-3706.

Nozoe, T. et al. Some synthetic applications of 3-carboxy-4-carboxymethyltropolone. *Tohoku Daigaku Hisui Yoeka Kagaku Kankyusho Hokoku* 1961, 10, 199-211.

Schneider, F. Synthese des D,L-imidazolyl-glycine and einiger derivate. *Hoppe-Seyler's Zeitxchrift Fuer Physiologie Chemie*, 1961, 324, 206-210.

What is claimed is:

1. An integrated photoactive analog of a non-photoactive bioactive small molecule, the analog being of the following formula, wherein:

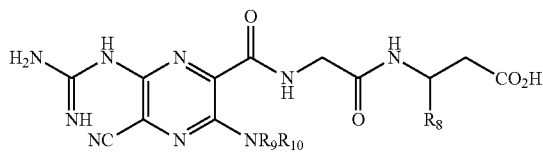

$R^8$ to $R^{10}$ are independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, or C1-C6 aminoalkyl.

2. The analog of claim 1, wherein each of $R^9$ and $R^{10}$ is hydrogen.

3. The analog of claim 1, wherein $R^8$ to $R^{10}$ are independently hydrogen or C1-C6 alkyl.

4. An integrated photoactive analog of a non-photoactive bioactive small molecule, the analog being of the following formula, wherein:

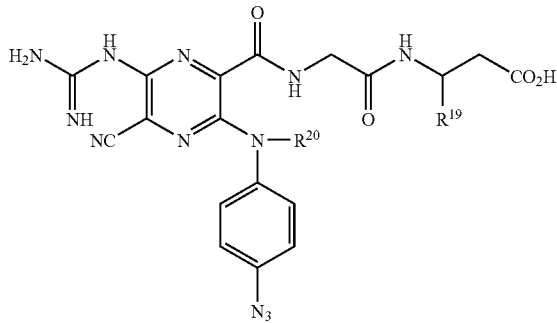

each of $R^{19}$ and $R^{20}$ is independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, or C1-C6 aminoalkyl.

5. An integrated photoactive analog of a non-photoactive bioactive small molecule, the analog being of the following formula, wherein:

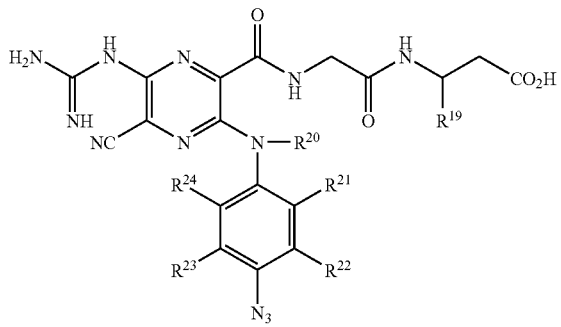

each of $R^{19}$ and $R^{20}$ is independently hydrogen, C1-C6 alkyl, C1-C6 acyl, C1-C6 alkoxycarbonyl, C1-C6 hydroxyalkyl, C1-C6 polyhydroxyalkyl, C1-C6 carboxyalkyl, or C1-C6 aminoalkyl; and $R^{21}$-$R^{24}$ are independently hydrogen, azide, azo, diazo, sulfenate, thiadiazole, peroxide, phthalocyanine, porphyrin, extended porphyrin, benzoporphyrin, or free radical or reactive intermediate forming groups thereof.

* * * * *